United States Patent [19]

Gubin et al.

[11] Patent Number: 5,739,340

[45] Date of Patent: Apr. 14, 1998

[54] INDOLIZINE DERIVATIVES WITH PHARMACEUTICAL ACTIVITY

[75] Inventors: Jean Gubin; Michel Renard, both of Brussels, Belgium

[73] Assignee: Elf Sanofi, Paris, France

[21] Appl. No.: 825,773

[22] Filed: Apr. 2, 1997

Related U.S. Application Data

[60] Continuation of Ser. No. 384,837, Feb. 7, 1995, abandoned, which is a division of Ser. No. 80,173, Jun. 23, 1993, Pat. No. 5,403,933.

[30] Foreign Application Priority Data

Jun. 23, 1992 [FR] France .................. 92 07663

[51] Int. Cl.⁶ .................. C07D 221/04; C07D 487/02
[52] U.S. Cl. .................. 546/183; 546/201; 546/277; 546/264; 546/266; 546/333; 548/453
[58] Field of Search .................. 548/453, 312.1; 546/277.1, 266, 201, 264, 183, 333

[56] References Cited

U.S. PATENT DOCUMENTS

| | | | |
|---|---|---|---|
| 4,957,925 | 9/1990 | Gubin et al. | 514/299 |
| 5,028,710 | 7/1991 | Gubin et al. | 546/183 |

FOREIGN PATENT DOCUMENTS

| | | |
|---|---|---|
| 0235111 | 9/1987 | European Pat. Off. . |
| 0302792 | 2/1989 | European Pat. Off. . |
| 0350384 | 1/1990 | European Pat. Off. . |
| 0382618 | 8/1990 | European Pat. Off. . |
| 0382628 | 8/1990 | European Pat. Off. . |
| 0382629 | 8/1990 | European Pat. Off. . |

*Primary Examiner*—Johann Richter
*Assistant Examiner*—Jane C. Oswecki
*Attorney, Agent, or Firm*—Jacobson, Price, Holman & Stern, PLLC

[57] ABSTRACT

The invention relates to indolizine derivatives of general formula:

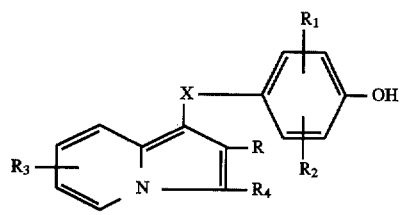

in which:

X denotes an —S or —$SO_2$— group, each of $R_1$ and $R_2$, which are identical or different, denotes hydrogen, the methyl or ethyl radical or a halogen atom, $R_3$ denotes hydrogen or a $C_1$–$C_4$ alkyl radical, $R_4$ denotes a precursor radical of a carboxyl group, R denotes a $C_1$–$C_6$ alkyl, $C_3$–$C_6$ cycloalkyl or phenyl radical, and their use as intermediates for the preparation of pharmaceutically active aminoalkoxybenzenesulphonylindolizine derivatives.

3 Claims, No Drawings

INDOLIZINE DERIVATIVES WITH PHARMACEUTICAL ACTIVITY

This application is a continuation of application Ser. No. 08/384,837, filed Feb. 7, 1995, which is a divisional of application Ser. No. 08/080,173, filed Jun. 23, 1993 now U.S. Pat. No. 5,403,933.

The present invention relates, in general, to new indolizine derivatives, to the process for preparing them and to their use as synthesis intermediates.

More precisely, the subject of the invention is indolizine derivatives of general formula:

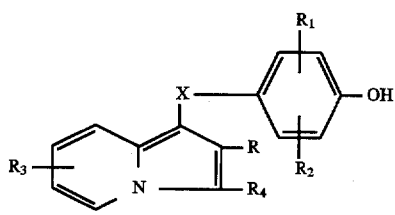    I in which:

X denotes an —S or —SO$_2$— group, each of $R_1$ and $R_2$, which are identical or different, denotes hydrogen, the methyl or ethyl radical or a halogen atom such as chlorine, bromine or iodine, R denotes a $C_1$–$C_6$ alkyl, $C_3$–$C_6$ cycloalkyl or phenyl radical, $R_3$ denotes hydrogen or a $C_1$–$C_4$ alkyl radical, $R_4$ denotes a precursor radical of a carboxyl group, such as a $C_1$–$C_4$ alkoxycarbonyl, aminocarbonyl or cyano radical.

Thus, taking the above values into account,

R can denote the methyl, ethyl, n-propyl, isopropyl, n-butyl, n-pentyl, n-hexyl or cyclopropyl radical, $R_3$ can denote especially the methyl, ethyl, n-propyl, isopropyl or n-butyl radical, $R_4$ can denote especially the methoxycarbonyl or ethoxycarbonyl radical.

The compounds of formula I in which each of $R_1$ and $R_2$ denotes hydrogen, $R_3$ denotes hydrogen or the methyl radical, $R_4$ denotes the methoxycarbonyl or cyano radical and R denotes the isopropyl or cyclopropyl radical constitute preferred compounds according to the invention.

The compounds of formula I in which X denotes the —SO$_2$— group can be denoted by the general formula:

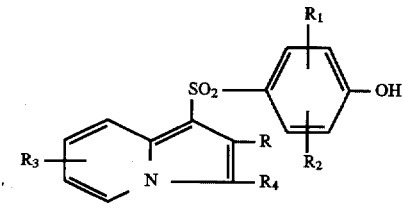    Ia in which R, $R_1$, $R_2$, $R_3$ and $R_4$ have the same meaning as above.

These compounds have been found to be particularly useful as intermediate products, especially for the preparation of 4-hydroxybenzenesulphonyl derivatives of general formula:

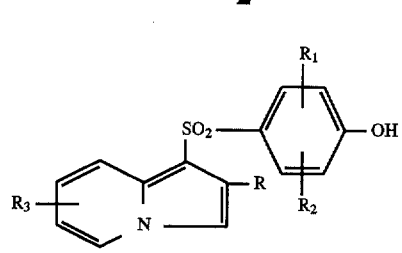    II in which R, $R_1$, $R_2$ and $R_3$ have the same meaning as above.

These compounds of formula II can themselves be widely employed as intermediates in the preparation of various products, especially for the final synthesis of aminoalkoxybenzenesulphonyl derivatives of general formula:

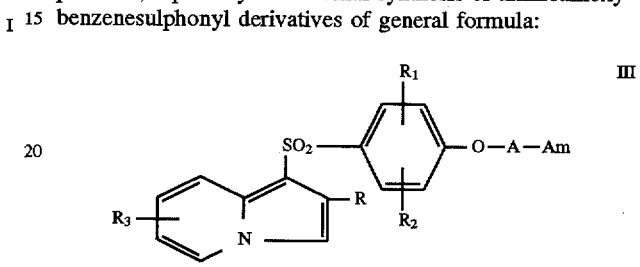    III in which R, $R_1$, $R_2$ and $R_3$ have the same meaning as above, A denotes a $C_2$–$C_5$ alkylene or 2-hydroxypropylene radical, and Am denotes a substituted amino radical, especially:

a radical of formula:

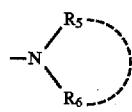

in which $R_5$ denotes hydrogen or a $C_1$–$C_8$ alkyl radical and $R_6$ denotes a $C_1$–$C_6$ alkyl radical or a radical of formula:

—Alk—$R_7$ in which Alk denotes a single bond or a $C_1$–$C_5$ alkylene radical and $R_7$ denotes a pyridyl, phenyl, 2,3-methylenedioxyphenyl, 3,4-methylenedioxyphenyl radical or a phenyl group substituted by one or a number of identical or different substituents selected from halogen atoms, $C_1$–$C_4$ alkyl groups or $C_1$–$C_4$ alkoxy groups, or $R_5$ and $R_6$, when taken together, denote a $C_3$–$C_6$ alkylene or alkenylene radical optionally interrupted by —O—, —NH, —N═ or —N—$R_8$, $R_8$ denoting a $C_1$–$C_4$ alkyl, phenyl or diphenylmethyl radical, with the result that $R_5$ and $R_6$, taken with the nitrogen atom to which they are attached, can denote especially a pyrrolidinyl, piperidinyl, morpholinyl, piperazinyl, 4-methylpiperazinyl, 4-phenylpiperazinyl or 1H-imidazolyl radical, a group of formula:

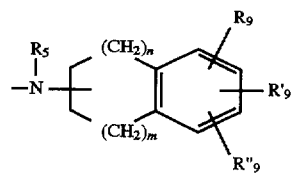

or

-continued

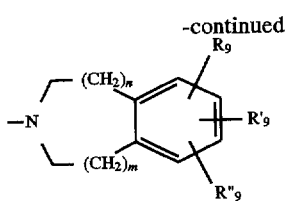

in which $R_5$ has the same meaning as above, each of $R_9$, $R'_9$ and $R''_9$, which are identical or different, denotes hydrogen, a halogen atom such as chlorine or bromine, a $C_1$-$C_4$ alkyl or $C_1$-$C_4$ alkoxy group, and each of n and m, which are identical or different, denotes 0, 1, 2 or 3, and for the preparation of their pharmaceutically acceptable salts.

Such aminoalkoxybenzenesulphonyl derivatives of formula III have been described especially in patents or patent applications EP-A-235,111, 302,793, 382,618, 382,628 and 382,629.

These compounds have been found particularly advantageous for their therapeutic applications, especially owing to their properties of inhibiting calcium translocation, as well as their bradycardisant, hypotensive or antiadrenergic properties which make them useful in the treatment of certain pathological syndromes of the cardiovascular system, in particular in the treatment of angina pectoris, of hypertension, of arrhythmia and of cerebral circulatory insufficiency. In the antitumour field, these compounds are useful as synergisers of anticancer agents.

As compounds which are particularly representative of this series of aminoalkoxybenzenesulphonyl derivatives there may be mentioned:

2-isopropyl-1-[4-{3-[N-methyl-N-(3,4-dimethoxy-β-phenethyl)amino]propoxy}benzenesulphonyl]-indolizine or fantofarone (recommended INN) and its pharmaceutically acceptable salts, 2-isopropyl-8-methyl-1-[4-{3-[N-methyl-N-(3,4-dimethoxy-β-phenethyl)amino]propoxy}benzenesulphonyl]indolizine and its pharmaceutically acceptable salts (Compound A), 2-isopropyl-8-methyl-1-[4-{3-[N-methyl-N-(3,5-dimethoxy-β-phenethyl)amino]propoxy}benzenesulphonyl]indolizine and its pharmaceutically acceptable salts (Compound B), 2-isopropyl-8-methyl-1-{4-[3-(di-n-butylamino)propoxy]benzenesulphonyl}indolizine and its pharmaceutically acceptable salts (Compound C), 2-isopropyl-1-[4-{3-[N-methyl-N-(3,4,5-trimethoxy-β-phenethyl)amino]propoxy}benzenesulphonyl]indolizine and its pharmaceutically acceptable salts (Compound D), 2-isopropyl-8-methyl-1-{4-[3-(6,7-dimethoxy-1,2,3,4-tetrahydro-2-N-isoquinolinyl)propoxy]benzenesulphonyl}indolizine and its pharmaceutically acceptable salts (Compound E), 2-isopropyl-1-[4-{3-[N-methyl-N-(3,4-dimethoxybenzyl)amino]propoxy}benzenesulphonyl]indolizine and its pharmaceutically acceptable salts (Compound F), 2-isopropyl-5-methyl-1-[4-{3-[N-methyl-N-(3,4-dimethoxy-β-phenethyl)amino]propoxy}benzenesulphonyl]indolizine and its pharmaceutically acceptable salts (Compound G).

In patent EP-A-0,235,111 a process has been described for the preparation of derivatives of 1-benzenesulphonylindolizine, in this case 1-(4-hydroxybenzenesulphonyl)indolizines of formula II making use of the following reactions:

(a) coupling of 2-chloromethylpyridine with an alkali metal 4-tosyloxybenzenesulphinate according to the process described in J. Chem. Soc. 1965, p. 3090, which yields 2-(4-tosyloxybenzenesulphonylmethyl)pyridine, (b) cyclisation of this compound at reflux with an α-bromoketone, so as to give a 1-(4-tosyloxybenzenesulphonyl)indolizine, (c) hydrolysis of this indolizine derivative at reflux and in a basic medium so as to produce the desired 1-(4-hydroxybenzenesulphonyl)indolizines.

This method exhibits a number of disadvantages, the greatest of which can be summarised as follows:

need to prepare the alkali metal 4-tosyloxybenzenesulphinate by a process comprising a number of stages, for example by a four-stage process from phenol, consisting in preparing the alkali metal 4-hydroxybenzenesulphonate, in tosylating this compound, in forming the corresponding sulphonyl chloride and finally the alkali metal salt of the desired sulphinate derivative, use of an excess of α-bromoketone, a highly lachrymatory product contaminated with secondary products after preparation by bromination of a ketone, need to make use of reactions requiring elevated and prolonged heating, handling of large quantities of intermediate products because of the weight and the bulk of the protective tosyl group.

The investigation of an industrial process for the preparation of derivatives of 1-(4-hydroxybenzenesulphonyl)indolizine of formula II making use of synthesis intermediates to which access is easy and which are relatively inexpensive, with a satisfactory yield of final product, remains of an unquestionable interest.

The possibility of inducing the formation of the benzenesulphonyl group by oxidation of the benzenethio group is, furthermore, known. Nevertheless, this method has received little investigation within the scope of the oxidation of indolizine sulphides to corresponding sulphones, probably because of the well-known degradation of the indolizine ring under the effect of oxidising agents ("Heterocyclic Systems with Bridgehead Nitrogen Atoms", Part One, Intersc. Publ. New York, 1961, p. 263).

A process for the preparation of benzenesulphonylindolizines, namely 3-benzenesulphonylindolizines, calling for such a reaction of oxidation of the benzenethio group, has nevertheless been reported in patent FR-B-2,633,622.

According to this process, a 3-(4-hydroxy-benzenethio)indolizine derivative which is O-protected, especially by the methyl radical, is oxidised, by means of 3-chloroperbenzoic acid in basic medium, so as to obtain the desired benzenesulphonylindolizine derivatives. By way of example, this French patent reports the preparation of 2-isopropyl-3-(4-methoxybenzenesulphonyl)indolizine by oxidation of 2-isopropyl-3-(4-methoxybenzenethio)indolizine in a 53% yield.

This method is therefore characterised by the use of a stage of oxidation of a benzenethio derivative comprising a protected hydroxyl radical, such as a methoxy radical, a hydroxyl radical which it is necessary to modify in the continuation of the process, so as to regenerate the free hydroxyl.

This application according to an oxidation/deprotection pair can be explained by the fact that the free hydroxyl functional group is well known to be sensitive to oxidising agents, since it is capable of being oxidised quite easily (Methoden der Organischen Chemie (Houben-Weyl), Volume VI/1C—Phenole Part 2 page 1121).

Within the scope of the development of the present invention, attempts have been made to prepare 2-isopropyl-3-(4-hydroxybenzenesulphonyl)indolizine by starting with an indolizine derivative containing an unprotected hydroxyl radical, in this case 2-isopropyl-1-ethoxycarbonyl-3-(4-hydroxybenzenethio)indolizine, by the application of a process consisting in oxidising this 4-hydroxybenzenethio derivative and then deprotecting the 1-position of the indolizine.

To this end, 2-isopropyl-4-ethoxycarbonyl-3-(4-hydroxybenzenethio)indolizine was subjected to the action of 3-chloroperbenzoic acid in N,N-dimethylformamide. However, what was recorded was not the formation of the expected 2-isopropyl-1-ethoxycarbonyl-2-isopropyl-3-(4-hydroxybenzenesulphonyl)indolizine but, on the contrary, the presence of large quantities of starting material.

Now, it has surprisingly been found, according to the invention, that it is possible to obtain, in excellent yields, 1-(4-hydroxybenzenesulphonyl)indolizine derivatives by oxidation of a benzenethio group comprising not a protected hydroxyl group but the free hydroxyl group.

According to the invention the sulphonyl derivatives of formula I are prepared by oxidising a compound of formula I in which X denotes —S—, that is to say a benzenethio derivative of general formula:

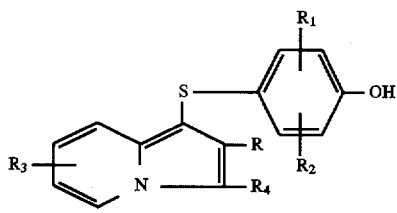

in which R, $R_1$, $R_2$, $R_3$ and $R_4$ have the same meaning as above, by means of an appropriate oxidising agent such as 3-chloroperbenzoic acid or magnesium monoperphthalate and in an appropriate solvent, and this yields the desired compounds.

The oxidation generally takes place at a temperature of between −5° C. and ambient temperature, preferably at a temperature between 0° C. and the ambient temperature.

As for the solvent, this may be a polar solvent containing an amide group, for example N,N-dimethylformamide, N,N-dimethylacetamide, 2-methylpyrrolidone or hexamethylphosphoramide, a $C_1$–$C_4$ alcohol, for example methanol or ethanol, or else a nitrile such as acetonitrile.

N,N-Dimethylformamide constitutes a particularly preferred solvent.

From 2 to 2.5 equivalents of oxidising agent, preferably 3-chloroperbenzoic acid or magnesium monoperphthalate, are generally employed per equivalent of compound of formula IV.

In addition, it is possible to envisage buffering the reaction mixture by introducing a weak base such as an alkali or alkaline-earth metal carbonate or bicarbonate.

The compounds of formula I in which X denotes an —$SO_2$— group can be synthesised very advantageously by starting with the compounds of formula IV.

In fact, the formation of a 4-hydroxybenzenesulphonyl chain from 4-hydroxybenzenethio derivatives of formula IV can be performed by making use of a single reaction, in contrast to the process of patent FR-B-2,633,622, which requires the use of a double reaction, that is to say first an oxidation and then a deprotection of the hydroxyl radical.

What is more, the compounds of formula IV make possible the synthesis of compounds of formula I, in extremely high yields, while avoiding the disadvantages of the previous techniques.

For example, 2-isopropyl-3-methoxycarbonyl-1-(4-hydroxybenzenesulphonyl)indolizine can be prepared from 2-isopropyl-3-methoxycarbonyl-1-(4-hydroxybenzenethio) indolizine, in yields of 75 to 80%, whereas 3-cyano-1-(4-hydroxybenzenesulphonyl)-2-isopropylindolizine can be obtained from 3-cyano-1-(4-hydroxybenzenethio)-2-isopropylindolizine in yields higher than 95%.

Consequently, another subject of the invention relates to the 4-hydroxybenzenethio derivatives of formula IV as new industrial products, especially as synthesis intermediates, for example for the preparation of the 4-hydroxybenzenesulphonyl derivatives of formula I.

The compounds of formula IV can be obtained by reacting an indolizine derivative of general formula:

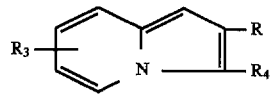

in which R, $R_3$ and $R_4$ have the same meaning as above, with a compound of general formula:

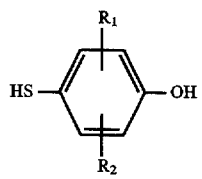

in which $R_1$ and $R_2$ have the same meaning as above, this being done in an appropriate solvent such as an aqueous solvent containing a $C_1$–$C_4$ alcohol, for example methanol, or an amide such as N,N-dimethylformamide or hexamethylphosphoramide, in the presence of iodine and preferably at the reflux temperature of the reaction mixture, to obtain the desired compounds.

The compounds of formula V and VI are known compounds which can be obtained by known methods.

For example, the indolizine derivatives of formula V can be obtained by making use of the following stages:

1) reaction of 2-picoline with a halide, preferably the bromide, of general formula:

in which $R_4$ has the same meaning as above and Hal denotes a halogen atom such as chlorine, bromine or iodine, to give a halide of 2-methylpicolinium derivative of general formula:

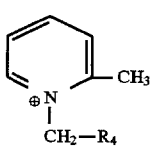

in which $R_4$ and Hal have the same meaning as above.

2) coupling of the halide of the 2-methylpicolinium derivative in question with an anhydride of general formula:

           IX in which R has the same meaning as above, the reaction taking place in an appropriate solvent, for example an aromatic hydrocarbon such as benzene or toluene, at the reflux temperature of the mixture and in the presence of an acid-scavenger such as an amine, for example triethylamine, and this yields the desired compounds.

As mentioned above, the (4-hydroxybenzenesulphonyl) indolizine derivatives of formula Ia can be employed for the preparation of indolizine derivatives of formula II.

Consequently, another subject of the invention relates to the preparation of indolizine derivatives of formula II by making use of a process according to which:

either a compound of formula Ia is treated in an appropriate solvent such as an alcohol, for example ethanol, at the reflux temperature of the mixture and in the presence of an alkali metal hydroxide such as sodium hydroxide, and the mixture is then acidified with a strong acid such as hydrochloric or sulphuric acid and is decarboxylated by heating to a temperature of 130° C. to 150° C., and this yields the desired compounds, or a compound of formula Ia in which $R_4$ denotes a cyano or aminocarbonyl radical is treated with a strong acid such as sulphuric acid and at the reflux temperature of the mixture, and this yields the desired compounds.

Thus, the use of a compound of formula Ia in which $R_4$ denotes especially a cyano or aminocarbonyl group makes possible a simplified implementation since, according to an alternative form of the process, a single stage turns out to be necessary for the removal of the cyano group, in contrast to the compounds of formula Ia in which $R_4$ denotes an alkoxycarbonyl group, which require saponification, acidifying and decarboxylation stages.

According to the invention the compounds of formula II can be obtained in high yields from the indolizine derivative of formula V via the compounds of formulae IV and Ia.

For example, 2-isopropyl-1-(4-hydroxybenzenesulphonyl)indolizine can be synthesised from 2-isopropyl-3-methoxycarbonylindolizine in an overall yield of 70%.

As indicated above, the 4-hydroxybenzenesulphonyl-indolizine derivatives of formula Ia can be employed for the preparation of the aminoalkoxybenzenesulphonyl derivatives of formula III.

Consequently, another subject of the invention relates to 4-hydroxybenzenesulphonyl derivatives of formula Ia as intermediates for the final synthesis of the aminoalkoxybenzenesulphonyl derivatives of formula III, in particular for the preparation of fantofarone and of Compounds A to G.

For example, the compounds of formula III can be prepared by starting with a 4-hydroxybenzenesulphonyl derivative of formula II, itself obtained according to the invention from a 4-hydroxybenzenesulphonyl derivative of formula Ia, by making use of a process comprising the following sequence of stages:

(a) coupling of the compound of formula II in the presence of a basic agent with a dihaloalkane of general formula:

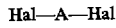 Hal—A—Hal           X in which A and Hal have the same meaning as above, this being done at reflux in an appropriate solvent, generally in a polar or apolar solvent such as methyl ethyl ketone, N,N-dimethylformamide, benzene, toluene or xylene, or else, (b1) the coupling of a halogenated alcohol of general formula:

 Hal—A—OH           XI in which A and Hal have the same meaning as above, this being done in a solvent such as N,N-dimethylformamide and in the presence of a basic agent, followed by coupling of the alcohol derivative obtained with a halide of general formula:

Hal—W           XII in which Hal has the same meaning as above and W denotes a $C_1$–$C_4$ alkylsulphonyl, for example methanesulphonyl, radical or $C_6$–$C_{10}$ arylsulphonyl, for example benzenesulphonyl or p-toluenesulphonyl, radical, in an acid-scavenging solvent, for example pyridine, or else, (b2) heating at reflux with an epihalohydrin such as epichlorohydrin or epibromohydrin, in the presence of a basic agent and in a polar solvent such as methyl ethyl ketone, to obtain the sulphonylindolizine derivatives of general formula:

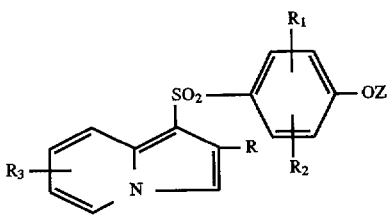           XIII in which R, $R_1$, $R_2$ and $R_3$ have the same meaning as above and Z denotes a radical of general formula:

 —A—$Z_1$ in which A has the same meaning as above and $Z_1$ denotes a halogen atom, a $C_1$–$C_4$ alkylsulphonyloxy or $C_6$–$C_{10}$ arylsulphonyloxy radical.

The basic agent employed during the treatment of the compound of formula II is generally an alkali metal carbonate, for example potassium carbonate, an alkali metal hydroxide such as sodium or potassium hydroxide, an alkali metal hydride such as sodium hydride or an alkali metal alcoholate, for example sodium methylate or ethylate.

The derivative of formula XIII is therefore reacted with an amine of general formula:

 H—Am           XIV in which Am has the same meaning as above, the reaction taking place in the presence of an acid-scavenger and in an appropriate solvent, generally a polar solvent such as an alcohol, for example butanol, a ketone such as methyl ethyl ketone, an aromatic hydrocarbon, for example benzene, toluene or xylene, or else an excess of amine of formula XIV, to obtain the compounds of formula III in the form of free base which, if desired, can be reacted with an appropriate acid to form a pharmaceutically acceptable salt of this compound.

According to an alternative method it is also possible to use the compounds of formula II by treating such a compound directly with a halide of general formula:

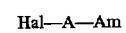 Hal—A—Am           XV in which Hal and Am have the same meaning as above and A denotes a $C_2$–$C_5$ alkylene radical, the reaction being conducted in the presence of a basic agent such as an alkali metal carbonate, for example potassium carbonate, an alkali metal hydroxide such as sodium or potassium hydroxide, an alkali metal hydride such as sodium hydride or an alkali metal alcoholate, for example sodium methylate or ethylate, to obtain the compounds of formula III, in which A denotes a $C_2$–$C_5$ alkylene radical which, if desired, can be reacted with an appropriate acid to form a pharmaceutically acceptable salt of this compound.

The following nonlimiting examples illustrate the preparation of the compounds of the invention:

Example 1

Preparation of 2-isopropyl-3-methoxycarbonyl-1-(4-hydroxybenzenethio)indolizine a) 1-Methoxycarbonylmethyl-2-methylpyridinium bromide 47.3 ml (76.5 g; 0.5 mol) of methyl bromoacetate are added to a solution of 49.3 ml (46.5 g; 0.5 mol) of 2-picoline in 50 ml of acetonitrile in a 500-ml round bottom flask. The addition is performed-dropwise and with stirring. After a few minutes the reaction becomes strongly exothermic and must be cooled with an ice bath. After three days' stirring the quaternary salt is precipitated with an addition of dry ethyl ether. The white powder thus obtained is filtered off, is washed with a little ethyl ether and is dried under vacuum in a desiccator containing phosphorus pentoxide.

119.93 g of 1-methoxycarbonylmethyl-2-methylpyridinium bromide are obtained in this way. Yield: 98%.

M.p.: 130° C.

b) 2-Isopropyl-3-methoxycarbonylindolizine 40 g (0.162 mol) of 1-methoxycarbonylmethyl-2-methylpyridinium bromide, 80.8 ml (77.2 g; 0.487 mol) of isobutyric anhydride and 16 ml of toluene are introduced successively into a 500-ml round bottom flask fitted with a condenser and placed under nitrogen. The suspension is stirred and 31.2 ml (22.8 g; 0.224 mol) of triethylamine are then added. The suspension immediately turns yellow in colour. It is heated progressively and with stirring to 120° C. After 5 hours reaction the mixture, which has become clear and homogeneous, is poured into 1 liter of iced water and is extracted three times with 250 ml of diethyl ether. The ether phase is washed with water and is dried over sodium sulphate, filtered, and the solvent is evaporated off in a rotary evaporator. The residue is then distilled under high vacuum (0.03 mm Hg). The first fraction at 40° C. makes it possible to recover the excess isobutyric anhydride, the desired product distilling between 120° C. and 123° C.

21.74 g of 2-isopropyl-3-methoxycarbonylindolizine are obtained in this way.

Yield: 62%.

B.p.: 120° C.–123° C. (0.03 mm Hg).

An additional test enabled a 76% yield to be obtained.

c) 2-Isopropyl-3-methoxycarbonyl-1-(4-hydroxybenzenethio)indolizine 5 g (0.023 mol) of 2-isopropyl-3-methoxycarbonylindolizine are dissolved in a mixture of 75 ml of N,N-dimethylformamide and 50 ml of water in a 250-ml round bottom flask placed under nitrogen.

The solution is placed under inert atmosphere and 3.15 g (0.025 mol) of 4-hydroxybenzenethiol predissolved in 25 ml of N,N-dimethylformamide are injected with a syringe. An immediate bleaching of the iodine is observed. The reaction is then stirred for 20 hours at ambient temperature. The reaction solution is poured into 500 ml of iced water and is extracted with two times 500 ml of ethyl ether. The ether phase is washed four times with water and once with a sodium thiosulphate solution. The ether phase is then seen to bleach and is then dried over sodium sulphate. After filtering, the solvents are evaporated under vacuum. 7.9 g of a yellowish crude product are thus recovered and this is purified by chromatography on a silica column (eluent: 30/70 ethyl acetate/heptane) (Rf of the initial indolizine derivative: 0.6; Rf of the desired compound: 0.3) or by recrystallisation from diisopropyl ether.

7.5 g of 2-isopropyl-3-methoxycarbonyl-1-(4-hydroxybenzenethio)indolizine are obtained in this way.

Yield: 96%.

M.p.: 162° C. (diisopropyl ether).

Example 2

Preparation of 2-isopropyl-3-methoxycarbonyl-1-(4-hydroxybenzenesulphonyl)indolizine 3.41 g (0.01 mol) of 2-isopropyl-3-methoxycarbonyl-1-(4-hydroxybenzenethio)indolizine are dissolved in 50 ml of N,N-dimethylformamide in a 250-ml round bottom flask. The reaction is stirred at 0° C. (ice bath) and 5.44 g (0.022 mol) of 3-chloroperbenzoic acid predissolved in 50 ml of N,N-dimethylformamide are then added. The addition is performed dropwise, very slowly (2 h 30 min) and the reaction is followed by thin layer chromatography (TLC) on silica (eluent: 70/30 ethyl acetate/heptane; Rf of the starting indolizine derivative: 0.8; Rf of the intermediate sulphoxide: 0.3; Rf of the desired compound: 0.5). As soon as half the quantity of 3-chloroperbenzoic acid (25 ml) is added, the starting compound is seen to disappear and quantitative formation of the intermediate sulphoxide is observed. The oxidation of the latter to sulphone is much slower and requires the reaction to be conducted at ambient temperature. After the end of the addition (2 h 30 min) the reaction is left with stirring and at ambient temperature for 20 hours. After 20 hours a TLC shows that some traces of intermediate sulphoxide still remain. 0.66 g (0.003 mol) of 3-chloroperbenzoic acid are then added again and stirring is continued for two hours. After this period and after a final TLC check, the solution, which has become reddish, is poured into 500 ml of iced water and the precipitation of the desired product is observed. After filtration and drying of the orange solid 4.26 g of crude reaction product are recovered. This is washed, with 100 ml of hot diisopropyl ether and is filtered off to recover a slightly brownish white solid which can be recrystallised from toluene.

2.8 g of 2-isopropyl-3-methoxycarbonyl-1-(4-hydroxybenzenesulphonyl)indolizine are obtained in this way.

Yield: 75%.

M.p.: 199° C. (toluene).

Example 3

Preparation of 3-cyano-1-(4-hydroxybenzenethio)-2-isopropylindolizine a) 1-Cyanomethyl-2-methylpyridinium chloride 16.2 ml (19.3 g; 0.25 mol) of 98% chloroacetonitrile are added dropwise to a solution of 24.6 ml (23.25 g; 0.25 mol) of 2-picoline in 50 ml of acetonitrile in a 250-ml round bottom flask. Stirring is then continued at reflux for 18 hours and the mixture is then cooled in an ice bath. The precipitate is filtered off and is washed twice with diethyl ether. The highly hygroscopic product thus obtained is then dried, in a vacuum desiccator in the presence of phosphorus pentoxide.

20.35 g of 1-cyanomethyl-2-methylpyridinium chloride are obtained in this way.

Yield: 48%.

b) 3-Cyano-2-isopropylindolizine 20.35 g (0.12 mol) of 1-cyanomethyl-2-methylpyridinium chloride, 12 ml of toluene and 62 ml (59 g; 0.36 mol) of 97% isobutyric anhydride are introduced successively into a 250-ml round bottom flask fitted with a condenser and kept under nitrogen. Triethylamine is added dropwise, with stirring. The mixture is heated progressively to 120° C. (bath temperature) and this temperature is maintained for 4 hours. The material is poured into iced water and is extracted three times with diethyl ether. The ether phase is washed with water, is dried over anhydrous sodium sulphate and is filtered. The solvent is evaporated off under vacuum and the excess isobutyric anhydride is then distilled off (approximately 45 ml). The residue is purified on a column of silica gel (750 g), eluting with a 75/25 mixture of heptane and ethyl acetate.

4 g of 3-cyano-2-isopropylindolizine are obtained in this way.

Yield: 18%.

c) 3-Cyano-1-(4-hydroxybenzenethio)-2-isopropylindolizine 3 g (0.0163 mol) of 3-cyano-2-isopropylindolizine are dissolved, under nitrogen, in a mixture of 50 ml of N,N-dimethylformamide and 36 ml of water in a 250-ml round bottom flask. 2.75 g (0.0196 mol) of 90% 4-hydroxybenzenethiol are added followed, dropwise, by a solution of 4.14 g (0.0163 mol) of iodine in 75 ml of N,N-dimethylformamide. Bleaching of the iodine is then observed. After stirring for 20 hours at ambient temperature the contents of the round bottom flask are poured into iced water.

The material is extracted with a mixture of diethyl ether and ethyl acetate and the organic layer is then washed with water. It is dried over anhydrous sodium sulphate, filtered, the solvent is evaporated under vacuum and the residue is purified on a column of silica gel (eluent: 60/40 heptane/ ethyl acetate).

3.6 g of 3-cyano-1-(4-hydroxybenzenethio)-2-isopropylindolizine are collected in this way and are recrystallised from toluene.

Yield: 72%.

M.p.: 160° C.

Example 4

Preparation of 3-cyano-1-(4-hydroxybenzenesulphonyl)-2-isopropylindolizine 3 g (0.0097 mol) of 3-cyano-1-(4-hydroxybenzenethio)-2-isopropylindolizine are dissolved in 150 ml of N,N-dimethylformamide. This solution is placed in an iced water bath and a solution of 4.78 g (0.0194 mol) of 70% 3-chloroperbenzoic acid in 90 ml of N,N-dimethylformamide is then added dropwise. The material is then stirred at ambient temperature for 20 hours and the contents of the flask are then poured into iced water. After stirring for 30 minutes, the precipitate formed is filtered off and is recrystallised from ethyl acetate.

3.18 g of 3-cyano-1-(4-hydroxybenzenesulphonyl)-2-isopropylindolizine are obtained in this way.

Yield: 96%.

M.p.: 232° C.

Example 5

Preparation of 2-isopropyl-3-methoxycarbonyl-1-(4-hydroxybenzenesulphonyl)indolizine 2 g (0.00586 mol) of 2-isopropyl-3-methoxycarbonyl-1-(4-hydroxyphenylthio)indolizine are dissolved in 45 ml of N,N-dimethylformamide. The reactor containing the mixture is then placed in an ice bath and a solution of 3.62 g (0.00586 mol) of 80% magnesium monoperphthalate hexahydrate (MMPP) in 40 ml of N,N-dimethylformamide is added dropwise. A check by thin layer chromatography on silica gel (TLC) (eluent: 1/1 heptane/ethyl acetate) after the addition of the MMPP shows that the sulphide has been converted into sulphoxide. After approximately 15 hours at ambient temperature a mixture of sulphone and of sulphoxide is observed by TLC. Cooling is applied and another 0.72 g (0.00116 mol) of MMPP in 20 ml of N,N-dimethylformamide are added. After a new period of approximately 15 hours at ambient temperature the mixture is poured into iced water and is extracted with diethyl ether. The organic layer is washed with water and dried over anhydrous sodium sulphate. After vacuum evaporation of the solvent a red oily product is obtained which is purified by chromatography on a silica column (eluent: 1/1 heptane/ ethyl acetate).

1.4 g of 2-isopropyl-3-methoxycarbonyl-1-(4-hydroxybenzenesulphonyl)indolizine are collected in this way.

Yield: 64%.

The following nonlimiting examples illustrate the use of the compounds of the invention.

Example A

Preparation of 2-isopropyl-1-(4-hydroxybenzenesulphonyl)indolizine 1.12 g (0.003 mol) of 2-isopropyl-3-methoxycarbonyl-1-(4-hydroxybenzenesulphonyl)indolizine are dissolved in 30 ml of hot ethanol in a 100-ml round bottom flask. 9 ml of a 1N aqueous solution of sodium hydroxide are added and the mixture is refluxed for 12 hours. The ethanol is then evaporated off and the salt obtained dissolved in 250 ml of iced water. The solution is neutralised with 1N hydrochloric acid to pH=1.

The intermediate acid precipitates. It is recovered by filtration, is dried and yields 1.08 g of a white solid. This is placed in a small reactor and heated for 2 hours at 140° C. under nitrogen. A slightly greenish powder is obtained, which is recrystallised from toluene.

0.927 g of 2-isopropyl-1-(4-hydroxybenzenesulphonyl) indolizine are obtained in this way.

Yield: 98%.

M.p.: 182° C. (toluene).

Example B

Preparation of 2-isopropyl-1-(4-hydroxybenzenesulphonyl)indolizine 0.3 g (0.0009 mol) of 3-cyano-1-(4-hydroxybenzenesulphonyl)-2-isopropylindolizine are heated for 48 hours at reflux (oil bath at 120° C.) in a mixture of 3 ml of acetic acid, 3 ml of water and 3 ml of concentrated sulphuric acid. The material is diluted with water and extracted with ethyl acetate. The extract is washed with water, dried over anhydrous sodium sulphate and the solvent is evaporated off under vacuum.

0.2 g of 2-isopropyl-1-(4-hydroxybenzenesulphonyl) indolizine are obtained in this way.

Yield: 70%.

Example C

Preparation of 2-isopropyl-1-[4-{3-[N-methyl-N-(3,4-dimethoxy-β-phenethyl)amino]propoxy}benzenesulphonyl]indolizine or fantofarone 0.015 mol of 1-chloro-3-[N-methyl-N-(3,4-dimethoxy-β-phenethyl)amino]propane and 0.018 mol of finely ground potassium carbonate are added to 0.012 mol of 2-isopropyl-1-(4-hydroxybenzenesulphonyl)indolizine in 100 ml of methyl ethyl ketone. The mixture is refluxed for 24 hours and is then returned to ambient temperature. The inorganic salts are filtered off and the filtrate is evaporated under water pump vacuum. An oil is obtained and is purified by chromatography on a dry column of alumina.

2-Isopropyl-1-[4-{3-[N-methyl-N-(3,4-dimethoxy-β-phenethyl)amino]propoxy}benzenesulphonyl]indolizine is obtained in this way.

M.p.: 82°–83° C. (diisopropyl ether/dichloromethane).

We claim:

1. A process for preparing an aminoalkoxybenzenesulphonyl compound of formula III comprising the steps of:

a) reacting an indolizine benzenethio derivative compound of the general formula:

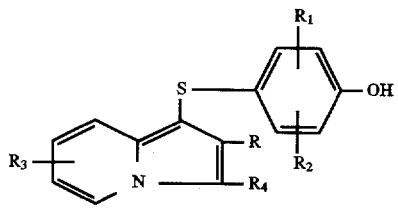

in which:

i) each of $R_1$ and $R_2$, which are identical or different, is selected from the group consisting of hydrogen, methyl, ethyl and halogen, ii) $R_3$ is selected from the group consisting of hydrogen and $C_1$–$C_4$ alkyl, iii) $R_4$ is selected from the group consisting of cyano, aminocarbonyl and $C_1$–$C_4$ alkoxycarbonyl, and iv) R is selected from the group consisting of $C_1$–$C_5$ alkyl, $C_3$–$C_6$ cycloalkyl, and phenyl, with an oxidizing agent selected from the group consisting of magnesium monoperphthalate and 3-chloroperbenzoic acid, to effect an indolizine compound of the formula:

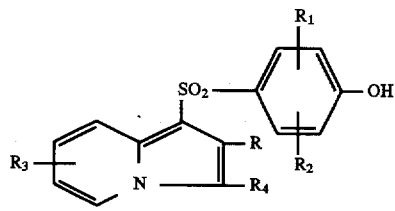

in which R, $R_1$, $R_2$, $R_3$ and $R_4$ have the same meaning as mentioned above; and b) affecting removal of the $R_4$ substituent,
when $R_4$ is a $C_1$–$C_4$ alkoxycarbonyl, by (i) heating at reflux temperature a mixture of the indolizine compound and an alkali metal hydroxide, followed by (ii) acidifying the mixture with a strong acid, and (iii) decarboxylation by heating the acidified mixture to a temperature of 130°–150° C., or
when $R_4$ is cyano or aminocarbonyl, heating at reflux temperature a mixture of the indolizine compound and a strong acid, resulting in a 4-hydroxybenzenesulphonyl intermediate having the formula:

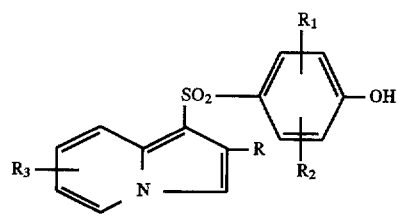

in which R, $R_1$, $R_2$ and $R_3$ have the same meaning as mentioned above;

c) reacting the intermediate with a halide of the general formula:

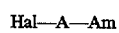

in which Hal represents halogen, A is $C_2$–$C_5$ alkylene, and Am is i) a radical of formula:

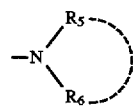

in which (A) $R_5$ denotes hydrogen or a $C_1$–$C_5$ alkyl radical and $R_6$ denotes a $C_1$–$C_8$ alkyl radical or a radical of formula:

in which Alk denotes a single bond or a $C_1$–$C_5$ alkylene radical and $R_7$ denotes pyridyl, phenyl, 2,3-methylenedioxyphenyl, 3,4-methylenedioxyphenyl, or phenyl substituted by one or more identical or different substituents selected from the group consisting of halogen, $C_1$–$C_4$ alkyl, and $C_1$–$C_4$ alkoxy, (B) $R_5$ and $R_6$ together denote $C_3$–$C_6$ alkylene or $C_3$–$C_6$ alkenylene, or (C) $R_5$ and $R_6$ together with the nitrogen atom to which they are attached denote pyrrolidinyl, piperidinyl, morpholinyl, piperazinyl, 4-methylpiperazinyl, 4-phenylpiperazinyl or 1H-imidazolyl, and ii) a radical of formula:

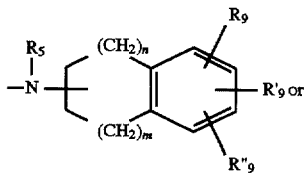

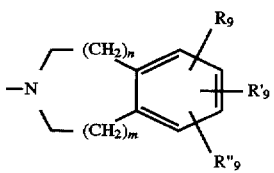

in which $R_5$ has the same meaning as above, each of $R_9$, $R'_9$ and $R''_9$, which are identical or different, denotes hydrogen, halogen, $C_1$–$C_4$ alkyl, or $C_1$–$C_4$ alkoxy, and each of n and m, which are identical or different, denotes 0, 1, 2 or 3;

in the presence of a basic agent selected from the group consisting of an alkali metal carbonate, an alkali metal hydroxide, an alkali metal hydride, and an alkali metal alcoholate to effect an aminoalkoxybenzenesulphonyl compound having the formula:

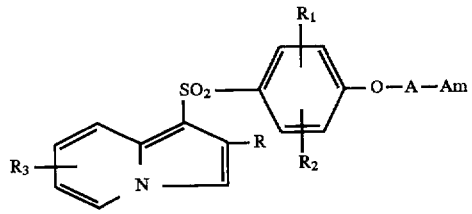

III in which each of R, $R_1$, $R_2$, $R_3$, A, and Am is as defined above, in the form of a free base; and, optionally, d) reacting the free base with an appropriate acid to form a pharmaceutically acceptable salt of the aminoalkoxybenzenesulphonyl compound.

2. Process of claim 1 wherein $R_4$ is a $C_1$–$C_4$ alkoxycarbonyl, and removal of the $R_4$ substituent is effected by (i) heating at reflux temperature a mixture of the indolizine compound and an alkali metal hydroxide, followed by (ii) acidifying the mixture with a strong acid, and (iii) decarboxylation by heating the acidified mixture to a temperature of 130°–150° C.

3. Process of claim 1 wherein $R_4$ is cyano or aminocarbonyl, and removal of the $R_4$ substituent is effected by heating at reflux temperature a mixture of the indolizine compound and a strong acid.

* * * * *